United States Patent [19]

Ohira

[11] Patent Number: 5,948,816
[45] Date of Patent: Sep. 7, 1999

[54] 4-SUBSTITUTED-2,7-DIDEOXY-7-FLUORO-2, 3-DIDEHYDRO-SIALIC ACID COMPOUNDS

[75] Inventor: Yutaka Ohira, Ibaraki, Japan

[73] Assignee: Daikin Industries, Ltd., Osaka, Japan

[21] Appl. No.: 09/068,646

[22] PCT Filed: Sep. 10, 1997

[86] PCT No.: PCT/JP97/03184
§ 371 Date: May 6, 1998
§ 102(e) Date: May 6, 1998

[87] PCT Pub. No.: WO98/11083
PCT Pub. Date: Mar. 19, 1998

[30] Foreign Application Priority Data

Sep. 10, 1996 [JP] Japan .................................. 8-238776

[51] Int. Cl.[6] .......................... A61K 31/35; C07D 413/02
[52] U.S. Cl. .......................... 514/459; 514/460; 548/239; 549/424; 549/425
[58] Field of Search .......................... 548/239; 514/374, 514/459, 460; 549/424, 425

[56] References Cited

U.S. PATENT DOCUMENTS 5,627,290  5/1997  Iida et al. .................................. 549/419

*Primary Examiner*—Amelia Owens
*Attorney, Agent, or Firm*—Knobbe, Martens, Olson & Bears, LLP

[57] ABSTRACT

Compounds represented by general formula (I) and salts thereof useful as non-tolerance-inducing antiviral agents, wherein A is O, $CH_2$ or S; $R^1$ is lower alkoxycarbonyl, or the like; $R^2$ is H, $OR^6$, F, Cl, Br, CN, $NHR^6$ or $SR^6$ (wherein R is H, $C_1$–$C_6$ lower alkyl and the like; one of $R^3$ and $R^{3'}$ is H and the other thereof is H, CN, anitrogenous group such as amino or the like; $R^4$ is $NHR^6$ or N=$CHR^6$; and $R^5$ is $CH_2CH_2XR^6$ or $CH(XR^6)CH_2XR^6$ (wherein X is O, S or NH.):

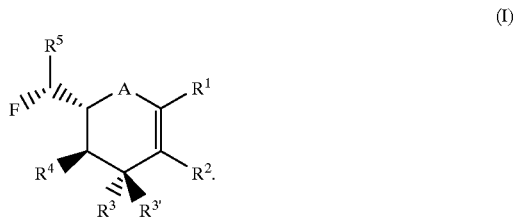

(I)

10 Claims, No Drawings

4-SUBSTITUTED-2,7-DIDEOXY-7-FLUORO-2, 3-DIDEHYDRO-SIALIC ACID COMPOUNDS

This is a 35 U.S.C. §371 application of PCT/JP97/03184, filed Sep. 10, 1997.

TECHNICAL FIELD

The present invention relates to N-acetylneuraminic acid derivatives whose hydroxyl group at 7-position is replaced by fluorine, synthetic intermediates thereof and use application thereof. The derivatives are useful as a sialidase inhibitor, an antiviral agent, an immunomodulating agent, an antitumor agent and like drugs.

BACKGROUND ART

Sialic acid (1)

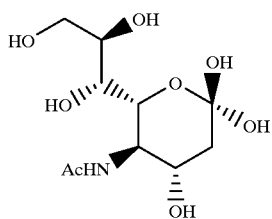

exists at a terminal of glycoproteins and glycolipids, and is involved in physiological activities of glycoproteins and glycolipids. Sialic acid derivatives are actively synthesized so as to clarify functions of sialic acid at a molecular level.

In particular, research and development of sialidase inhibitors are actively conducted as an agent for prophylaxis and therapy of influenza virus. Consequently, as effective sialidase inhibitor in vitro and in vivo, 4-amino- and 4-guanidino-2-deoxy-2,3-didehydrosialic acids (2 and 3)

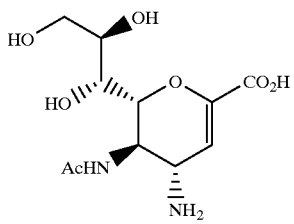

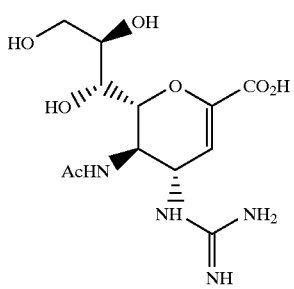

are reported (M. von Itzstein et al.: Nature, 363, 418–423 (1993); M. von Itzstein et al.: Carbohydrate Research, 259, 301–305 (1994); JP-A-5-507068). It is said that no drug-resistant virus will appear at first with respect to the derivatives. However, development of highly active compounds without cross-resistance is desired, since it is well predictable that drug-resistant viruses will appear clinically.

In addition, 7-fluoro-2,7-dideoxy-2,3-didehydrosialic acid is reported (international publication WO95/32955). However, sialidase inhibiting activities thereof are not disclosed.

7-fluorosialic acid derivatives of said compound whose hydroxyl group at 4 position is substituted has not been synthesized and will be useful as a drug, since the substitution is thought to affect physiological activities thereof.

Objects of the invention relate to 4-substituted-2,7-dideoxy-7-fluoro-2,3-didehydro-sialic acids which are expected as drugs such as an antiviral agent, an immunomodulating agent and an antitumor agent, synthetic intermediates thereof and use application thereof.

DISCLOSURE OF THE INVENTION

As a result of research to synthesize sialic acid analogs which are chemically modified at side chain by fluorine, the present inventors succeeded synthesis of said analogs. Thus, the present invention has been accomplished.

The present invention relates to a compound represented by formula (I)

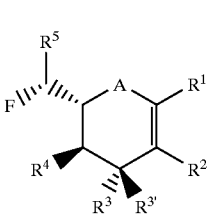

(I)

wherein

A is O, $CH_2$ or S.

$R^1$ represents a lower alkoxy carbonyl group, COOH, $PO(OH)_2$, $SO_3H$ or a tetrazole group.

$R^2$ represents a hydrogen atom, $OR^6$, F, Cl, Br, CN, $NHR^6$ or $SR^6$ (wherein $R^6$ represents a hydrogen atom, an optionally substituted $C_1$–$C_6$ lower alkyl group, a $C_1$–$C_4$ lower acyl group or an optionally substituted aryl group.

One of $R^3$ and $R^{3'}$ represents a hydrogen atom, and the other represents a hydrogen atom, a nitrile group, an optionally substituted amino group, an azido group, a lower alkylthio group, an amidino group, a formamidino(—$N=CHNH_2$) group, a cyanoamidino group or a guanidino group.

$R^4$ represents $NHR^6$, $N=CHR^6$ (wherein R is as defined above.).

$R^5$ represents $CH_2CH_2XR^6$ or $CH(XR^6)CH_2XR^6$ (wherein X represents an oxygen atom, a sulfur atom, a NH group, $R^6$ is as defined above.). and salts thereof.

The invention preferably relates to a compound of formula (II)

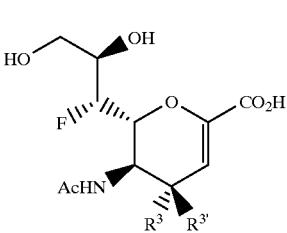

(II)

wherein $R^3$ and $R^{3'}$ are as defined above and salts thereof.

The invention more preferably relates to a compound represented by formula (III)

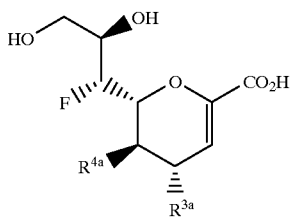

(III)

wherein
$R^{3a}$ represents a hydrogen atom, a nitrile group, an optionally substituted amino group, an azido group, a lower alkylthio group or a guanidino group.
$R^{4a}$ is $NHCOR^7$ (wherein $R^7$ represents a hydrogen atom, an optionally substituted $C_1$–$C_6$ alkyl group or an optionally substituted aryl group,
and salts thereof.

The invention, more preferably, relates to 2,3-didehydrosialic acid derivatives represented by chemical formula (IV) and (V)

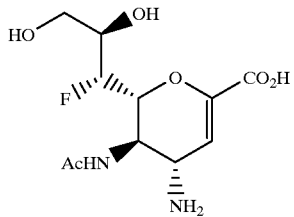

(IV)

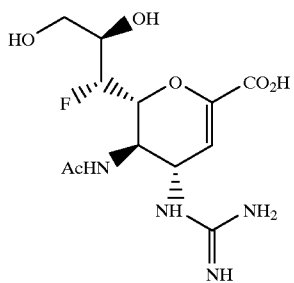

(V)

wherein Ac represents an acetyl group.
The invention further relates to a synthetic intermediate represented by formula (VI)

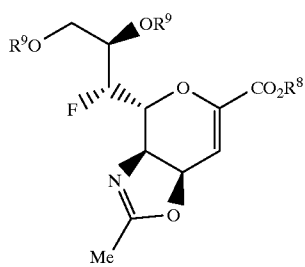

(VI)

wherein $R^8$ represents a lower alkyl group or a benzyl group. $R^9$ represents a hydroxyl protective group.

The compounds (I) to (V) correspond to 4-substituted-2,3-didehydrosialic acid derivatives whose hydroxyl group at 7-position is fluorinated. The compounds are not described in the literature.

The compound (VI) corresponds to a synthetic intermediate of compounds (I) to (V). The compound is not described in the literature.

With respect to the compound of formula (I), A is O, $CH_2$ or S, preferably O.

$R^1$ represents a lower alkoxy carbonyl group, COOH, $PO(OH)_2$, $SO_3H$ or a tetrazole group. Lower alkoxy carbonyl groups include straight or branched alkoxycarbonyl groups having 2 to 5 carbon atoms, such as methoxycarbonyl, ethoxycarbonyl, n-propoxycarbonyl, isopropoxycarbonyl, n-butoxycarbonyl, sec-butoxycarbonyl, isobutoxycarbonyl and tert-butoxycarbonyl.

$R^2$ represents a hydrogen atom, $OR^6$, F, Cl, Br, CN, $NHR^6$ or $SR^6$.

$R^6$ represents a hydrogen atom, an optionally substituted $C_1$–$C_6$ lower alkyl group, a $C_1$–$C_4$ lower acyl group or an optionally substituted aryl group. $C_1$–$C_6$ lower alkyl groups include methyl, ethyl, n-propyl, isopropyl, n-butyl, sec-butyl, isobutyl, tert-butyl, pentyl, hexyl, etc. Substituents of substituted $C_1$–$C_6$ lower alkyl groups include a hydroxyl group, a halogen atom (F, Cl, Br, I), a lower alkoxy group (methoxy, ethoxy, n-propoxy, isopropoxy, n-butoxy, sec-butoxy, isobutoxy, tert-butoxy). $C_1$–$C_4$ lower acyl groups include formyl(HCO), acetyl, propionyl, butyryl, isobutyryl. Aryl groups include a phenyl group, a naphtyl group, a pyridyl group. Substituents of substituted aryl groups include a hydroxyl group, a lower alkyl group (methyl, ethyl, n-propyl, isopropyl, n-butyl, isobutyl, sec-butyl, tert-butyl), a lower alkoxy group (methoxy, ethoxy, n-propoxy, isopropoxy, n-butoxy, isobutoxy, sec-butoxy, tert-butoxy), nitro, amino, mono-loweralkyl(methyl, ethyl, n-propyl, isopropyl, n-butyl, isobutyl, sec-butyl, tert-butyl) substituted amino, di-loweralkyl(methyl, ethyl, n-propyl, isopropyl, n-butyl, isobutyl, sec-butyl) substituted amino, a halogen atom (F, Cl, Br, I), a trifluoromethyl group.

One of $R^3$ and $R^{3'}$ represents a hydrogen atom, and the other represents a hydrogen atom, nitrile, an optionally substituted amino group, azido, a lower alkylthio, amidino, formamidino(—N═$CHNH_2$), cyanoamidino or guanidino. Optionally substituted amino groups include amino($NH_2$), mono-loweralkyl(methyl, ethyl, n-propyl, isopropyl, n-butyl, isobutyl, sec-butyl, tert-butyl) substituted amino, di-loweralkyl(methyl, ethyl, n-propyl, isopropyl, n-butyl, isobutyl, sec-butyl) substituted amino, piperidino, pyrrolidinyl, morpholino, piperazinyl, N-methylpiperazinyl and like cyclic amino groups, anilino, cyclohexylamino, hydroxylamino, a lower alkoxy amino(methoxyamino, ethoxyamino, n-propoxyamino, isopropoxyamino, n-butoxyamino, isobutoxyamino, sec-butoxyamino, tert-butoxyamino), hydrazino, 1-monolower alkyl(methyl, ethyl, n-propyl, isopropyl, n-butyl, isobutyl, sec-butyl, tert-butyl) hydrazino, 2-monolower alkyl(methyl, ethyl, n-propyl, isopropyl, n-butyl, isobutyl, sec-butyl, tert-butyl)hydrazino, 2-di-lower alkyl(methyl, ethyl, n-propyl, isopropyl, n-butyl, isobutyl, sec-butyl)hydrazino. Lower alkylthio groups include $C_1$–$C_4$ lower alkylthio group such as methylthio, ethylthio, n-propylthio, isopropylthio, n-butylthio, sec-butylthio, isobutylthio, tert-butylthio.

$R^4$ represents —$NHR^6$ or N═$CHR^6$ (wherein $R^6$ is as defined above.).

$R^5$ represents $CH_2CH_2XR^6$ or $CH(XR^6)CH_2XR^6$ (wherein X represents an oxygen atom, a sulfur atom or a NH group. $R^6$ is as defined above.).

$R^{3a}$ represents a hydrogen atom, a nitrile group, an optionally substituted amino group, an azido group, a lower alkylthio group or a guanidino group.

$R^{4a}$ is NHCOR$^7$ (wherein R$^7$ represents a hydrogen atom, an optionally substituted $C_1$–$C_6$ alkyl group or an optionally substituted aryl group.). Optionally substituted $C_1$–$C_6$ alkyl groups and optionally substituted aryl group represented by R$^7$ are the same as examples of said R$^6$.

R$^8$ represents methyl, ethyl, n-propyl, isopropyl, n-butyl, sec-butyl, isobutyl, tert-butyl, pentyl, hexyl and like a $C_1$–$C_6$ lower alkyl group or a benzyl group.

Hydroxyl protective groups represented by R9 include acetyl, propionyl, butyryl, isobutyryl, valeryl, isovaleryl, pivaloyl and like a $C_2$–$C_5$ lower acyl group, methoxycarbonyl, ethoxycarbonyl, n-propoxycarbonyl, isopropoxycarbonyl, n-butoxycarbonyl, sec-butoxycarbonyl, isobutoxycarbonyl, tert-butoxycarbonyl and like a lower alkoxycarbonyl group, benzyl and benzoyl group.

R$^1$ is preferably a lower alkoxy carbonyl group or COOH, more preferably COOH.

R$^2$ is preferably a hydrogen atom.

R$^6$ is preferably a hydrogen atom and a $C_1$–$C_6$ lower alkyl group, more preferably a hydrogen atom.

R$^3$ and R$^{3'}$ are preferably: R$^{3'}$ is a hydrogen atom, and R$^3$ is an optionally substituted amino, amidino, formamidino, cyanoamidino or guanidino; more preferably R$^{3'}$ is a hydrogen atom, and R$^3$ is an optionally substituted amino or guanidino; most preferably R$^{3'}$ is a hydrogen atom, and R$^3$ is amino or guanidino.

R$^4$ is preferably —NHR$^6$, more preferably acetylamino group.

R$^5$ is preferably CH(OH)CH$_2$OH

R$^{3a}$ is preferably an amino group, a guanidino group.

R$^{4a}$ is preferably NHCOMe in case that R$^7$ is methyl.

R$^8$ is preferably methyl, ethyl, n-propyl, isopropyl, n-butyl, sec-butyl, isobutyl, tert-butyl, pentyl, hexyl and like a $C_1$–$C_6$ lower alkyl group, more preferably methyl or ethyl.

R$^9$ is preferably acetyl, propionyl, benzyl and benzoyl, more preferably acetyl.

4-substituted-2,3-didehydrosialic acid derivatives are important compounds showing sialidase inhibiting activities. Fluorine-substituted 4-substituted-2,3-didehydrosialic acid is useful for applications of practical drug development and clinical chemistry.

Therefore, provision of practical amount of 4-substituted-2,3-didehydro-7-fluorosialic acid has great significance.

Production of the compounds of the invention are described below.

Reaction Scheme 1

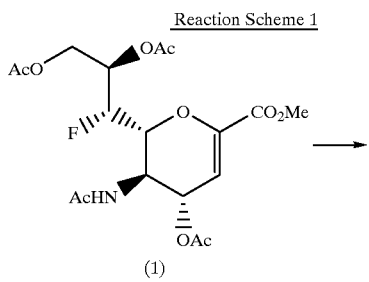

(1)

-continued

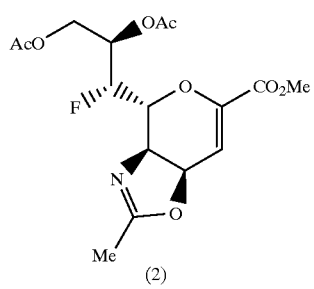

(2)

An oxazoline form (2) of fluorine-containing 2,3-didehydrosialic acid derivative represented by formula (I) may be synthesized, according to reaction scheme 1, by treating compound (1) with trifluoroborate 5 ether complex. The starting material of the reaction scheme 1 may be easily synthesized according to a method described in international publication WO95/32955.

Reaction Scheme 2

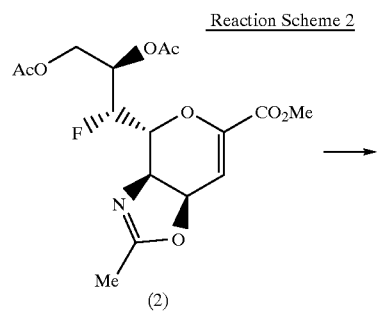

(2)

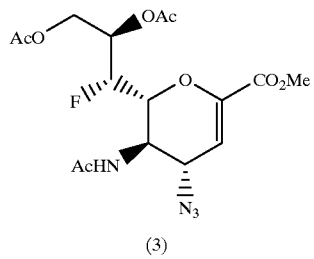

(3)

A 2,3-didehydrosialic acid derivative (3) represented by formula (I) may be obtained, as shown in scheme 2, by treating the sialic acid derivative (2) prepared as shown above with trimethylsilylazide (TMSN$_3$).

Reaction Scheme 3

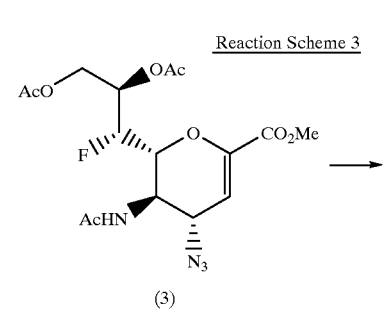

(3)

-continued

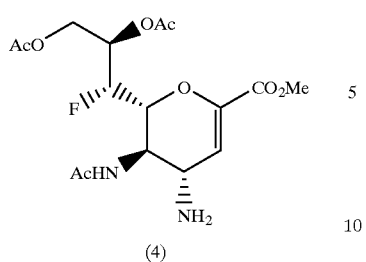
(4)

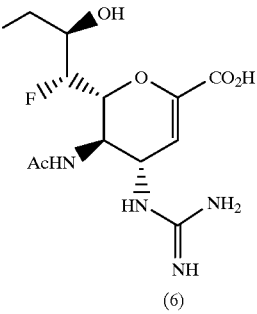
(6)

A compound (4) represented by formula (I) may be obtained by hydrogenation of compound (3) in the presence of palladium-carbon in toluene-methanol as shown in scheme 3. Reduction may be carried out using hydrogen sulfide.

Reaction Scheme 4

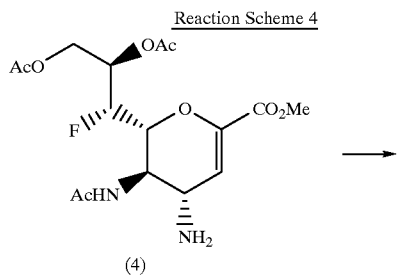
(4)

↓

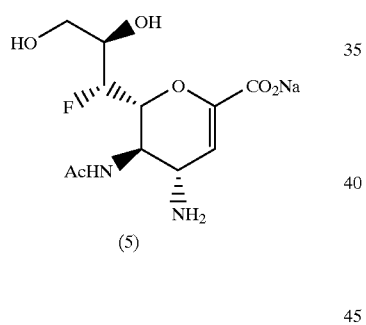
(5)

A fluorine-substituted 2,3-didehydrosialic acid derivative (5) represented by chemical formula (IV) may be obtained by deprotection of compound (4) prepared as shown above. Deprotection may be carried out, for example, by reacting the compound at room temperature for 1 to 24 hours in NaOH/MeOH.

Reaction Scheme 5

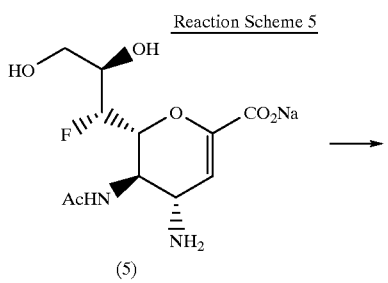
(5)

↓

A fluorine-substituted 2,3-didehydrosialic acid derivative (6) may be obtained by converting an amino group of compound (5) thus obtaind into a guanidino group using aminoiminosulfonic acid according to reaction scheme 5.

Aminoiminosulfonic acid used therein was easily synthesized according to a method described in Tetrahedron Letters, 29, 3183–3186 (1988).

The compounds of the invention having a variety of $R^3$ and $R^{3'}$ may be prepared by converting the azido compound (3) used as a starting material.

The compound of the invention represented by formula (I) may be synthesized according to reaction formula (A) in conditions similar to said reaction schemes 1–5. A starting compound (1A) may be easily produced according to the literatures such as M. von Itzstein et al.: Nature, 363, 418–423(1993); M. von Itzstein et al.: Carbohydrate Research, 259, 301–305 (1994); JP-A-5-507068; International Publication WO95/32955.

Reaction Formula (A)

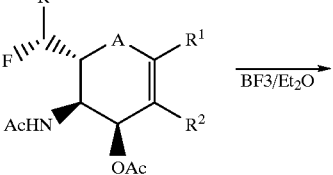
(1A)

$\xrightarrow{BF_3/Et_2O}$

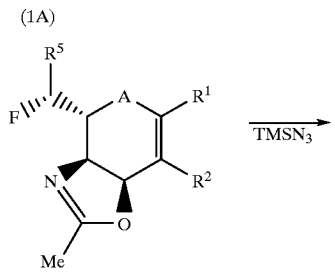
(2A)

$\xrightarrow{TMSN_3}$

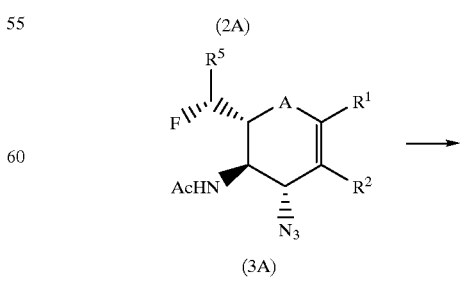
(3A)

→

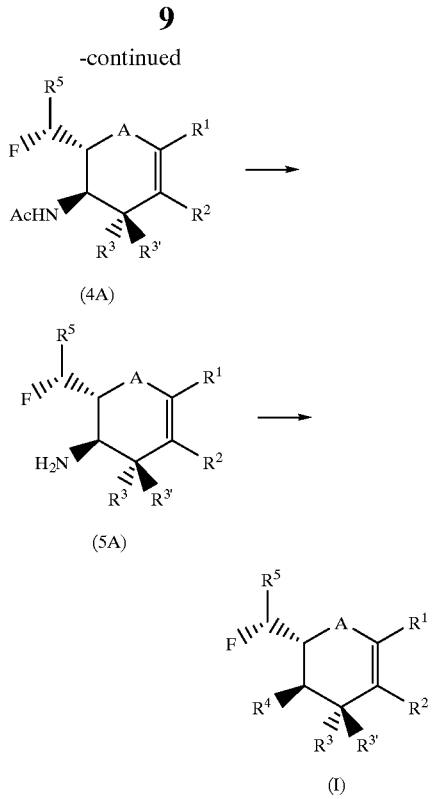

wherein A, $R^1$, $R^2$, $R^3$, $R^{3'}$, $R^4$ and $R^5$ are as defined above.

Compounds of formulae (2A) and (3A) are obtained by reacting a starting compound of formula (1A) in conditions similar to reaction schemes 1 and 2. An azido group of compound of formula (3A) may be converted into CN by a reaction with KCN; may be converted into a lower alkylthio group by a reaction with $NaSR^a$ ($R^a$ represents a lower alkyl group); may be converted into an amino group by reduction according to reaction scheme 3. After conversion of azido group of the compound of formula (3A) into an amino group, the amino group may be converted into an amidino group, a formamidino group, a cyanoamidino group, a guanidino group, etc. according to conventional methods.

The compound of formula (4A) thus obtained may be converted into the compound of formula (5A) by deacetylation with an acid or a base. Subsequently, the compound of formula (5A) may be converted into compound of formula (I) by alkylation, acylation, arylation, or a reaction with $O=CHR^6$.

The salts of the compound of the invention include sodium, potassium and like alkaline metal salts; hydrochloric acid, sulfuric acid, phosphoric acid, nitric acid and like inorganic acid salts; methansulfonic acid, p-toluenesulfonic acid and like sulfonic acid salts, maleic acid, fumaric acid, malic acid and like organic acid salts. The salts may be prepared according to a conventional method.

The compound of the invention together with suitable carriers, excipients, diluents may be made into various dosage forms such as tablets, injections, suppositories, ointments, creams, inhalations, nasal sprays, lotions and so on, as an agent for prophylaxis or therapy of influenza virus infection. Such preparations can be formulated in a manner already known or conventional to those skilled in the art.

When oral solid preparations are formulated, tablets, granules, powders, capsules may be produced according to a conventional method by optionally adding to the compound of the invention excipients, binders, disintegrators, lubricants, coloring agents, flavors etc. Such additives are conventionally used in the art. For example, excipients include lactose, sucrose, sodium chloride, glucose, starch, calcium carbonate, kaolin, microcrystalline cellulose and silicic acid; binders include water, ethanol, propanol, simple syrup, glucose solution, starch solution, gelatin solution, carboxymethyl cellulose, carboxypropyl cellulose, hydroxypropyl starch, methyl cellulose, ethyl cellulose, shellac, calcium phosphate and polyvinyl pyrrolidone; disintegrators include dried starch, sodium alginate, agar powder, sodium bicarbonate, calcium carbonate, sodium lauryl sulfate, stearic acid monoglyceride and lactose; lubricants include purified talc, stearic acid salts, borax and polyethylene glycol; flavors include sucrose, bitter orange peel, citric acid and tartric acid.

When oral liquid preparations are formulated, liquids for internal use, syrups and elixirs may be produced according to a conventional method by adding to the compound of the invention flavors, buffers (sodium citrate etc.), stabilizers (tragacanth, arabic gum, gelatin etc.) and so on.

When injections are prepared, subcutaneous, intramuscular and intravenous injections may be produced according to a conventional method by adding to the compound of the invention pH adjusting agents, buffers, stabilizers, isotonicities, local anesthetics, etc. The pH adjusting agents and buffers include sodium citrate, sodium acetate, sodium phosphate etc. Stabilizers include sodium pyrosulfite, EDTA, thioglycolic acid, thiolactic acid. Local anesthetics include procaine hydrochloride and lidocaine hydrochloride.

When suppositories are prepared, suppositories may be produced according to a conventional method by adding to the compound of the invention known carriers in the art such as polyethylene glycol, lanolin, cacao butter, fatty acid triglycerides, optionally Tween (trademark) and like surfactants.

The amount of the compound of the present invention to be incorporated into each of the dosage units varies with the symptoms of the patient or with the type of the preparations. The preferable amount per administration unit is about 0.1–10 mg for nasal sprays, about 0.1–1 mg for injections. The dosage per day of the compound in the above dosage form is variable with the symptoms, body weight, age, sex and other factors of the patient, but usually ranges about 0.2–15 mg for human adult. The preparation is preferably administered in a single dose or in two to four devided doses.

The compounds of the present invention having potent physiological activities as antiviral agent are useful as an agent for treating viral infection, an agent for prophylaxis and therapy of viral disorders.

In addition, the compounds of the present invention are useful as antitumor agents and immunomodulating agents.

Examples are described below. The invention is in no way limited by the examples.

BEST MODE FOR CARRYING OUT THE INVENTION

EXAMPLE 1

Synthesis of 2-Methyl-(methyl 8,9-di-O-acetyl-2,6-anhydro-7-fluoro-3,5,7-trideoxy-D-glycero-D- talo-non-2-enonate)-[4,5-d]-2-oxazoline (hereinafter, Compound (2a))

0.81 g (1.87 mmol) of methyl 5-acetamide-4,8,9- tri-O-acetyl-2,6-anhydro-3,5,7-trideoxy-7-fluoro-D- glycero-D-galacto-non-2-enonate (hereinafter, Compound (1a)) was dissolved in dry dichloromethane (12 ml) under argon atmosphere. Dry methanol (75 ml, 1.86 mmol) was added thereto and ice-cooled. Trifluoroborane ether complex (2.3 ml, 18.7 mmol) was added dropwise thereto, and the reaction mixture was stirred at room temperature (29° C.) for 13 hours. The reaction mixture was poured into a mixed solution of ice-cooled water-ethyl acetate-sodium carbonate (15 ml:50 ml:3 g). An aqueous layer was extracted with ethyl acetate. The organic layers were combined, washed with saturated brine and dried on magnesium sulfate. After concentration under reduced pressure, the residue was purified by flash chromatography (eluate: hexane:ethyl acetate=1:1) to give compound (2a) (352 mg, 50.4%).

$C_{16}H_{20}NO_8F(373.31)$ $[\alpha]_D^{25}=-20.4°$ (c=1.16, chloroform) IR(KBr) $\nu$ max cm$^{-1}$: 1730(ester) $^1$H-NMR (CDCl$_3$; TMS): $\delta$ 6.14(d, 1H, $J_{3,4}$=4.5Hz, H-3), 5.48(m, 1H, H-8), 5.02(ddd, 1H, $J_{6,7}$=1.5Hz, $J_{7,8}$=7.3Hz, $J_{H-7,F}$=45.3Hz, H-7), 4.89(dd, 1H, $J_{3,4}$=4.5Hz, $J_{4,5}$=9.1Hz, H-4), 4.76(ddd, 1H, $J_{9',8}$=2.2Hz, $J_{9,9'}$=12.5Hz, $J_{H,F}$=2.4Hz, H-9'), 4.31(dd, 1H, $J_{4,5}$=$J_{5,6}$=9.1Hz, H-5), 4.26(ddd, 1H, $J_{9,8}$=5.1Hz, $J_{9,9'}$=12.5Hz, $J_{H,F}$=2.2Hz, H-9), 3.80(3H, s, CO$_2$Me), 3.31(ddd, 1H, $J_{5,6}$=9.1Hz, $J_{6,7}$=1.5Hz, $J_{H,F}$=27.3Hz, H-6), 2.03, 2.06, 2.09(3s, 9H, 2OAc, Me) $^{19}$F-NMR(CDCl$_3$; CFCl$_3$): $\delta$ -212 (ddd, $J_{F,7H}$=45.3Hz, $J_{F,6H}$=27.3Hz, $J_{F,8H}$=11.8Hz, 1F, 7-F). Mass Spectrometry: m/z $C_{16}H_{21}NO_8F$ Calculated 374.1251 (M+H) Found 374.1246.

EXAMPLE 2
Synthesis of Methyl 5-acetamide-8,9-di-O- acetyl-2,6-anhydro-4-azido-7-fluoro-3,4,5,7-tetradeoxy-D- glycero-D-galacto-non-2-enonate (hereinafter, Compound (3a))

0.33 g (0.884 mmol) of compound (2a) was dissolved in dry tert-butanol (10 ml) under argon atmosphere. Azidotrimethylsilane (1.7 ml, 12.8 mmol) was added thereto and stirred with heat at 80° C. for 14 hours. The residue after concentration under reduced pressure was purified by flash chromatography (eluate: hexane:ethyl acetate=1:2) to give compound (3a) (335 mg, 91.0%).

$C_{16}H_{21}N_4O_8F(416.36)$ $[\alpha]_D^{25}=+80.8°$ (c=0.72, chloroform) IR(KBr) $\nu$ max cm$^{-1}$: 3500–3300(NH), 2110 (azido), 1750(ester). $^1$H-NMR(CDCl$_3$; TMS): $\delta$ 6.14(d, 1H, $J_{5,NH}$=7.4Hz, NH), 5.97(d, 1H, $J_{3,4}$=2.7Hz, H-3), 5.44(m, 1H, H-8), 4.83(ddd, 1H, $J_{6,7}$=1.9Hz, $J_{7,8}$=7.1Hz, $J_{H,F}$=38.9Hz, H-7), 4.42(dd, 1H, $J_{3,4}$=2.7Hz, $J_{4,5}$=8.8Hz, H-4), 4.71(ddd, 1H, $J_{9',8}$=2.4Hz, $J_{9,9'}$=12.3Hz, $J_{H,F}$=2.4Hz, H-9'), 4.22(ddd, 1H, $J_{9,8}$=5.3Hz, $J_{9,9'}$=12.3Hz, $J_{H,F}$=1.8Hz, H-9), 3.80(3H, s, CO$_2$Me), 3.62(m, 1H, H-5), 2.06, 2.06, 2.07(3s, 9H, 2OAc, NAc). $^{19}$F-NMR(CDCl$_3$; CFCl$_3$): $\delta$ -212(ddd, $J_{F,7H}$=38.9Hz, $J_{F,6H}$=27.3Hz, $J_{F,8H}$=11.8Hz, 1F, 7-F). Mass Spectrometry: m/z $C_{16}H_{22}N_4O_8F$ Calculated 417.1422 (M+H) Found 417.1424.

EXAMPLE 3
Synthesis of Methyl 5-acetamide-8,9-di-O- acetyl-4-amino-2,6-anhydro-7-fluoro-3,4,5,7-tetradeoxy-D- glycero-D-galacto-non-2-enonate (hereinafter, Compound (4a))

0.193 g (0.464 mmol) of compound (3a) was dissolved in a mixed solvent of dry methanol (8 ml) and dry toluene (6 ml). 10% palladium-carbon (42 mg) and acetic acid (40 ml, 0.699 mmol) was added thereto, and the mixture was stirred under atomospheric hydrogen atmosphere at room temperature for 30 minutes. After filtering the reaction mixture using Celite, Celite was washed with a mixed solvent of dry methanol-dry toluene (4:3). The filtrate and wash liquid were combined and concentrated under reduced pressure. The residue was purified by flash chromatography (eluate: ethyl acetate:isopropanol:water=5:3:1) to give compound (4a) (126 mg, 69.6%).

$C_{16}H_{23}N_2O_8F(390.37)$ $[\alpha]_D^{25}=+23.6°$ (c=0.62, chloroform) IR(neat) $\nu$ max cm$^{-1}$: 3350(amine), 1740 (ester). $^1$H-NMR(CDCl$_3$-CD$_3$OD=1:1; TMS): $\delta$ 5.94(d, 1H, $J_{3,4}$=2.5Hz, H-3), 5.42(m, 1H, H-8), 4.76(ddd, 1H, $J_{6,7}$=1.3Hz, $J_{7,8}$=6.5Hz, $J_{H,F}$=45.7Hz, H-7), 4.75(ddd, 1H, $J_{9',8}$=2.2Hz, $J_{9,9'}$=12.5Hz, $J_{H,F}$=2.4Hz, H-9'), 4.30(ddd, $J_{6,7}$=1.2Hz, $J_{5,6}$=10.2Hz, $J_{H,F}$=27.4Hz, H-6), 4.23(ddd, 1H, $J_{9,8}$=6.0Hz, $J_{9,9'}$=12.5Hz, $J_{H,F}$=1.7Hz, H-9), 3.80(3H, s, CO$_2$Me), 3.71–3.87(m, 2H, H-4, H-5), 2.05, 2.07, 2.08(3s, 9H, 2OAc, NAc). $^{19}$F-NMR(CDCl$_3$-CD$_3$OD=1:1; CFCl$_3$): $\delta$ -213(ddd, $J_{F,7H}$=45.1Hz, $J_{F,6H}$=27.3Hz, $J_{F,8H}$=12.7Hz, 1F, 7-F). Mass Spectrometry: m/z $C_{16}H_{24}N_2O_8F$ Calculated 391.1517 (M+H) Found 391.1520.

EXAMPLE 4
Synthesis of 5-Acetamide-4-amino-2,6-anhydro- 7-fluoro-3,4,5,7-tetradeoxy-D-glycero-D-galacto-non-2- enonic acid Sodium salt (hereinafter, Compound (5a))

36 mg (92 mmol) of compound (4a) was dissolved in dry methanol under argon atmosphere. 0.2 g of dried Amberlite IRA-410(OH$^-$) was added thereto. Immediately after stirring at room temperature for 1 hour, the mixture was spontaneously filtered through filter paper. The filter paper was washed with methanol. The filtrate and wash liquid were combined and concentrated under reduced pressure, and further dried in vacuo. The residue was dissolved in 1 ml of 0.15M sodium hydroxide and stirred at room temperature for 2 hours. The reaction solution was adjusted to a pH of 7.5 by adding Dowex50WX8(H$^+$), and filtered spontaneously. The filtrate was freeze-dried to give compound (5a) (9 mg, 31.1%).

$C_{11}H_{16}N_2O_6FNa(314.25)$ $[\alpha]_D^{25}=+3.4°$ (c=0.23, water) IR(KBr) $\nu$ max cm$^{-1}$: 3400(amine), 1600(carboxylate). $^1$H-NMR(D$_2$O; TSP): $\delta$ 5.75(d, 1H, $J_{3,4}$=2.3Hz, H-3), 3.88 (ddd, 1H, $J_{9,9'}$=12.3Hz, $J_{9',8}$=2.7Hz, $J_{H,F}$=2.7Hz, H-9'), 3.73 (ddd, 1H, $J_{9,9'}$=12.3Hz, $J_{9,8}$=5.1Hz, $J_{H,F}$=2.4Hz, H-9), 2.10 (s, 3H, AcN). $^{19}$F-NMR(D$_2$O; CFCl$_3$): $\delta$-208(dd, $J_{F,7H}$= 45.1Hz, $J_{F,6H}$=27.3Hz, 7-F). Mass Spectrometry: m/z $C_{11}H_{17}N_2O_6FNa$ Calculated 315.0969 (M+H) Found 315.0958.

EXAMPLE 5
Synthesis of 5-Acetamide-2,6-anhydro-7- fluoro-4-guanidino-3,4,5,7-tetradeoxy-D-glycero-D- galacto-non-2-enonic acid (hereinafter, Compound (6a))

34 mg (108 mmol) of compound (5a) was dissolved in water (1 ml). 40 mg (322 mmol) of aminoiminomethanesulfonic acid and 54 mg (391 $\mu$mol) of potassium carbonate was added thereto. The mixture was stirred at 34° C. for 12.5 hours. The reaction mixture was subjected to an Amberlite IRA-120B(H$^+$) column. Gradient elution was conducted by changing concentration of eluate from water to 0.6M aqueous triethylamine solution and finally 1.2M aqueous triethylamine solution to give crude compound (6a). The product was dissolved in water and isopropanol was added thereto to give crystalline compound (6a) (23 mg, 79.3%).

$C_{12}H_{19}N_4O_6F(334.30)$ $[\alpha]_D^{25}=+13.90$ (c=0.11, methanol) $^1$H-NMR(D$_2$O; TSP): $\delta$ 5.51(d, 1H, $J_{3,4}$=2.3Hz, H-3), 3.88(ddd, 1H, $J_{9,9'}$=12.3Hz, $J_{9',8}$=2.7Hz, $J_{H,F}$=2.7Hz, H-9'), 3.73(ddd, 1H, $J_{9,9'}$=12.3Hz, $J_{9,8}$=5.1Hz, $J_{H,F}$=2.4Hz, H-9), 2.10(s, 3H, AcN). $^{19}$F-NMR(D$_2$O; CFCl$_3$): $\delta$-208(dd, $J_{F,7H}$=45.1Hz, $J_{F,6H}$=27.3Hz, 7-F). Mass Spectrometry: m/z $C_{12}H_{20}N_4O_6F$ Calculated 335.1367 (M+H) Found 335.1384.

Pharmacological Test Example
1) Materials
  (i) Aqueous inhibitor solution
    Standard compounds, 2,3-didehydrosialic acid and 4-amino-2,3-didehydrosialic acid were synthesized according to methods described in the literatures (Carbohydrate Research, 186, 326(1989) and Carbohydrate Research, 259, 301(1994)). 7-Fluoro-2,3-didehydrosialic acid (7F-NeuAc-2-en) was synthesized according to a method described in WO95/32955. In addition, 4-amino-7-fluoro-2,3-didehydrosialic acid (4A-7F-NeuAc-2-en) obtained in example 5 was used as an inhibitor.

(ii) Aqueous substrate solution

A 10 μmol/ml of α 2-3 sialyl-lactose (product of Sigma) solution was used.

(iii) Buffer solution 0.1 mmol/ml of aqueous acetic acid solution (pH 5.2).

(iv) Enzyme solution

Influenza virus A/PR/8/34 was given as a gift by professor Yasuo SUZUKI, Department of Biochemistry, School of Pharmaceutical Science, University of Shizuoka. The virus was added to a reaction solution at a final concentration of 1.0 μg/10 μl.

2) Methods

The buffer solution (6 μl), aqueous inhibitor solution (2 μl), aqueous substrate solution (1 μl) and enzyme solution (1 μl) were added to a test tube which was kept at 37° C. for 10 minutes. After inactivation of the enzyme by dipping the test tube into a boiling water bath for 1 minute, the solution was spotted on silica gel 60 plate (Art 5721, Merck) and developed in isopropanol-28% aqueous ammonia-water (6:2:1, v/v). After development, the plate was dried by warmed air from dryer. A resorcinol hydrochloride reagent was sprayed thereon and then color development of sialic acid was determined with densitometer (Shimazu CS-910). Free sialic acid was determined at a 530 nm of measured wavelength and 430 nm of control wavelength. Inhibitory activity (%) was calculated by the equation {1−((molar amount of free sialic acid in the presence of inhibitor)/(molar amount of free sialic acid in the absence of inhibitor))}×100. Each concentration of inhibitors showing 50% inhibitory activity ($IC_{50}$) was shown in table 1.

TABLE 1

| Compound | $IC_{50}(\mu M)$ |
| --- | --- |
| 2,3-Didehydrosialic acid (NeuAc-2-en) | 12.0 |
| 7-Fluoro-2,3-didehydrosialic acid (7F-NeuAc-2-en) | 2.9 |
| 4-Amino-2,3-didehydrosialic acid (4A-NeuAc-2-en) | 1.5 |
| 4-Amino-7-fluoro-2,3-didehydrosialic acid (4A-7F-NeuAc-2-en) | 0.5 |

As shown in table 1, 4-amino-7-fluoro-2,3-didehydrosialic acid of the invention demonstrates a very potent sialidase inhibitory activity and is useful as an agent for prophylaxis or therapy of influenza virus infection.

I claim:

1. A compound represented by formula (I) or a salt thereof (I)

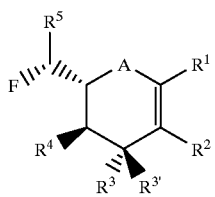

wherein A is O, $CH_2$ or S; $R^1$ represents a lower alkoxy carbonyl group, COOH, $PO(OH)_2$, $SO_3H$, or a tetrazole group; $R^2$ represents a hydrogen atom, $OR^6$, F, Cl, Br, CN, $NHR^6$, or $SR^6$, wherein $R^6$ represents a hydrogen atom, a substituted or unsubstituted $C_1$–$C_6$ alkyl group, a $C_1$–$C_4$ acyl group, or a substituted or unsubstituted aryl group; one of $R^3$ or $R^{3'}$ represents a hydrogen atom, and the other one represents a hydrogen atom, nitrile, a substituted or unsubstituted amino group, an azido group, a lower alkylthio group, an amidino group, a formamidino group, a cyanoamidino group, or a guanidino group; $R^4$ represents $NHR^6$ or $N=CHR^6$, wherein $R^6$ is as defined above; and $R^5$ represents $CH_2CH_2XR^6$ or $CH(XR^6)CH_2XR^6$, wherein X represents an oxygen atom, a sulfur atom, or a NH group, and $R^6$ is as defined above.

2. A compound according to claim 1 represented by formula (II)

(II)

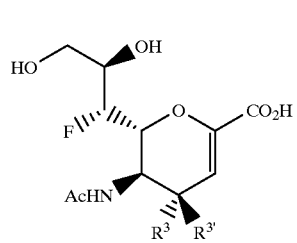

wherein $R^3$ and $R^{3'}$ are as defined above, Ac is an acetyl group, or a salt thereof.

3. A compound according to claim 1, which is represented by formula (III) or a salt thereof wherein $R^{3a}$ represents a hydrogen atom, a nitrile group, a substituted or unsubstituted amino group, an azido group, a lower alkylthio group, or a guanidino group; and $R^{4a}$ is $NHCOR^7$, wherein $R^7$ represents a hydrogen atom, a substituted or unsubstituted $C_1$–$C_6$ alkyl groups or a substituted or unsubstituted aryl group.

4. A compound according to claim 1 represented by the following formula (IV) or (V)

(IV)

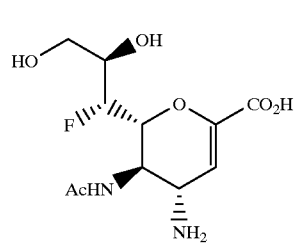

(V)

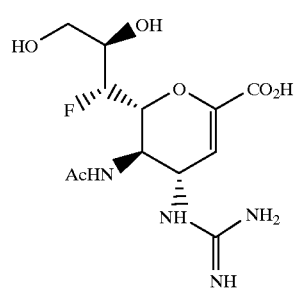

wherein Ac is an acetyl group, or a salt thereof.

5. A compound according to claim 1 represented by the following formula (VII) or (VIII)

(VII)

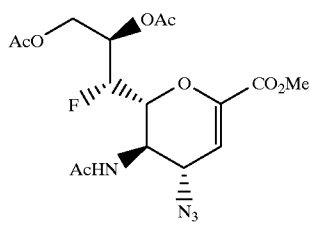

(VIII)

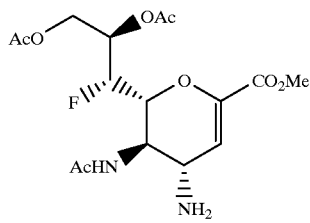

wherein Ac represents an acetyl group, or a salt thereof.

6. A synthetic intermediate represented by the following formula (VI)

(VI)

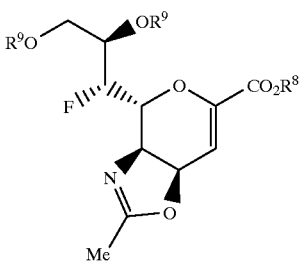

wherein $R^8$ represents a lower alkyl group or a benzyl group; and $R^9$ represents a hydroxyl protective group.

7. A pharmaceutical composition comprising the compound or a salt thereof according to claim 1 in an amount effective to exhibit a pharmaceutical effect, and a pharmaceutically acceptable carrier.

8. A pharmaceutical composition according to claim 7, wherein said pharmaceutical effect is a sialidase inhibitory effect.

9. A pharmaceutical composition according to claim 7, wherein said pharmaceutical effect is a prophylactic or therapeutic effect on influenza virus infection.

10. A method for preventing or treating influenza virus infection comprising administering a compound or a salt thereof according to claim 1 to a patient being susceptible to or having influenza virus infection.

* * * * *